United States Patent [19]

Strem

[11] Patent Number: 4,717,735

[45] Date of Patent: Jan. 5, 1988

[54] COMPOSITION FOR BODY WRAP

[75] Inventor: Richard C. Strem, Reno, Nev.

[73] Assignee: European Body Wrap, Inc., Sparks, Nev.

[21] Appl. No.: 850,138

[22] Filed: Apr. 10, 1986

[51] Int. Cl.$^4$ .............................................. A61L 15/03
[52] U.S. Cl. .................................... 424/447; 424/154;
514/949
[58] Field of Search ................. 514/949; 424/154, 447

[56] References Cited

U.S. PATENT DOCUMENTS

| | | | |
|---|---|---|---|
| 3,519,711 | 7/1970 | Svigals | 424/154 X |
| 4,059,700 | 11/1977 | Lindsay | 514/949 X |
| 4,637,933 | 1/1987 | Zabotto et al. | 514/949 X |

Primary Examiner—Leonard Schenkman
Attorney, Agent, or Firm—Mark C. Jacobs

[57] ABSTRACT

A composition for use in the practice of body wrapping, which composition when applied by a body wrapping technique to the skin, will extract waste products and toxins through the pores of the skin cells. Composition includes at least one clay and various inorganic salts.

7 Claims, No Drawings

COMPOSITION FOR BODY WRAP

BACKGROUND OF THE INVENTION

Body wrapping, the art of covering the human body with gauze bandages has been practiced in both the U.S.A. and Europe for many years. In Europe the bandages are covered with clay or mud, or the mud can be applied to the body without being applied to bandages hence the name mud baths.

Here in the U.S.A., wrapping has been used to achieve "instant weight loss". Practitioners of such art have been successful in achieving large body weight drops due to the fact that only water or excess water has been removed from the body. In the trade, these are referred to as "party wraps" due to the fact that oft times people want to look thin for a social occasion, but often a few rounds of drinks on the big night, all of the weight from liquid has been restored.

The instant invention categorically does not try to achieve weight loss. The instant invention pertains to a "detoxifying" composition and to the process that utilizes same to firm, tone and tighten soft tissue.

There is indeed a need for a procedure to extract the toxins and waste of the body through the pores of the skin.

One object of this invention is to provide a new body wrap composition.

Another object is to provide a process for applying the novel composition to the surface of the skin to extract waste products.

Yet another object is to provide a method of firming and tightening the elastin of the skin, and the elasticin of the soft tissues.

Still another object of the invention is to provide a technique for size reduction of the bust, waist, hips and other body sections without any substantial weight loss to the body.

A further object is to provide a means of firming the body texture that will last up to about one year.

These and other objects of the invention will in part be obvious and will in part appear hereinafter.

The invention accordingly comprises the several steps and the relation and order of one or more of such steps with respect to each of the others, and the composition possessing the features, properties and the relation of components which are exemplified in the following detailed disclosure and the scope of the application of which will be indicated in the claims.

For a fuller understanding of the nature and objects of the invention, reference should be made to the following detailed description.

SUMMARY OF THE INVENTION

A composition of a clay selected from the group consisting of bentonite and montmorillonite and various inorganic salts, which when applied to gauze bandages and wrapped around body parts draws out or extracts body wastes and toxins thereby firming, and tightening the soft tissue without any substantial body weight loss.

The process of wrapping the human body comprises utilizing the compositions of this manner as a soak for bandages which are then wrapped while warm about the various parts of the body.

DESCRIPTION OF THE PREFERRED EMBODIMENT

As a preface to the description of this invention, let it be known that applicant makes no health claims about this invention. He merely purports to set forth his novel composition and the use thereof and to report the results of such usage.

The compositions of this invention include at least one drawing clay. That is a clay selected from the group consisting of bentonite and montmorillonite. About 2 parts of the drawing clay are utilized in a composition that include approximately 2 parts magnesium sulfate, about 1 part magnesium chloride and about ¼ part sodium chloride, and a minor amount of zinc oxide all measured by volume to yield a body "pack" of 2¼ lbs by weight of total ingredients.

To prepare the compositions of the instant invention, all of the dry ingredients are pre-weighed out and then mixed at ambient temperature with about 2 gallons of water to yield a slurry of the desired composition. While the term slurry may be chemically correct, in layman's terms the consistency resembles a milkshake. From time to time it may be advantageous to re-stir the large vessel into which the bandages or wraps as they are called, are placed to soak up the Extractant. Preferably these are elasticized in nature the initial combination of ingredients in the amounts aforesaid and the water in the amount of about 2 gallons constitutes what I deem to be a body pack. That is, ample stock to carry on one full body wrap session.

The slurry and the wraps are placed in a hydroculator and heated to about boiling to ensure sterility and to aid in the absorption of the chemicals into the wraps. It is then allowed to cool to a temperature comfortable for handling. The wrapping comprises taking the moist bandages from the vessel and placing them, wet around the various body parts and pulling them such that there is a tight fit of the individual wraps to the body parts. Usually it takes about 40-60 wraps to cover the entire body, depending upon body size.

Many times however, the toning or tightening is to take place at only one section of the body, and thus only that portion of the body is wrapped.

An inch or even more, up to a maximum of about 3 inches over a series of time spaced wrapping sessions, can be removed from the bust, underbust, rib cage, waist, abdomen and buttocks of an average size women by firming, toning and tightening the soft tissue. In my experience, the softest tissue responds most to the process of this invention.

The maximum amount of dimension removable can not be predetermined by any calculation or observation, or appropriate determination. Only after two wrapping sessions have been completed, and the dimension reduction discerned for each of the two sessions can one estimate how worthwhile if at all a third or a fourth wrapping session will be. The decision is based on whether or not the point of maximized results has already been reached from the sessions already carried out.

It is again important to note, that even though reduction of body dimension is being achieved, it is being achieved without significant actual weight loss.

Compared to other industry wide techniques, the dimensions achievable by the use of the wrapping solution of this invention compared to wrapping solution s of the prior art, indicates that what we can achieve in 3 weeks oft times takes the competition 13 visits to the studio.

The mode of wrapping the body that we employ is generally similar to the procedure carried out in Europe. The bandages are placed on the body and allowed to dwell for about 60–70 minutes after the wrapping has been completed. These bandages upon removal all contain the body wastes and toxins that have been drawn out through the pores of the skin. They bandages must therefore be laundered before being put back into usage.

In the actual procedure, all wrapping is carried out toward the heart. Body wrapping starts at the feet and ankles and moves toward the heart. The same is true measuring from the hands and wrists back toward the heart. To do the abdomen, the technician uses a crisscross technique to achieve a tight support package, almost girdle—like in fashion, for lifting, shaping and firming. On the legs however, we employ a helical spiral wrapping technique. After the actual tight wrapping has taken place, the party puts on an exercise suit over the wrap to keep the body warm. He or she then proceeds to perform supervised exercises for a period of time while the Extractant is working. Any weight loss that may occur is purely incidental and unintentional, as the purpose of this total process is to firm, form and tighten soft tissue. The skin feels softer and more supple. Such weight loss is extremely minimal.

The preferred bandages to be employed are the elastic Ace bandages, since they permit the technician to achieve a tight wrap. A typical vendor of such a product is F. B. Titus & Son of Los Angeles Calif., among others.

While I have spoken of dissolving the ingredients at ambient temperature, I have found that temperatures closer to body temperature given less shock to the skin, i.e. are quite comfortable on the body. Thus I attempt to keep the vessel in the 85 to 90 degree F. range.

In order to replenish the strength of the Extractant, upon completion of a wrap session, a Pack, ie. 50% of the previous dry ingredients are mixed with 1 gallon of water and returned to the original vessel.

In my experience, I have found that it is beneficial not to open the pores by taking a hot bath or shower for up to four days after the completion of the wrap session. This gives the toxins an opportunity to accumulate beneath the surface of the skin as a result of the session. When the participant takes a hot shower, black and filth come out through the pores.

The materials being extracted comprise waste products and toxins that have accumulated in the cells, and which are not excreted as perspiration.

While the amounts set forth supra and infra are utilized in the preparation of a single body pack, I have found that it is preferred to start a wrap solution with a dual pack, ie double the amounts of dry ingredients in the amount of fluid for a single pack. Such procedures renders the replenishment aspect easier, in that a single pack formulation will readily replenish the solution to achieve full results.

Since the wrapping of the known lady is size dependent, the amount of fluid necessary to add to a single pack (dry ingredients) will vary. In practice it is only necessary to replenish to the 1 and ½ to 2 and ½ gallon level, rather than always adding two (2) full gallons to any one replenishment.

In order to show the effects of the procedure, I suggest taking body measurements, at set locations both before and after the wrap session. Usually up to 3 sessions will maximize the cumulative results potentially available.

In making the measurements noted above, actual markings are made in the body to make size change readily verifiable.

In the preparation of the Extractant composition of this invention, I have previously set forth the preferred amounts of each ingredient to make up a Pack (treatment for one person). While the results are not as good, I have found that I can employ each of the ingredients in the following ranges:

| Bentonite | 0 to 2.5 |
| --- | --- |
| Montmorillonite | 2.5 to 0 |
| Sodium Chloride | ¼ to ¾ |
| Magnesium chloride | ¾ to 1.25 |
| Magnesium Sulfate | 1.5 to 2.5 |
| Zinc Oxide | less than .001 |

All parts set forth are by volume. It is to be noted that the bentonite and the montmorillonite may be used separately or in combination in a range of 1.5 to 2.5 parts, but that at least the minimum of of these must be included in the formulation.

The dry ingredients in the proportions set forth above, constitute a "single pack", which single pack is mixed with 1.5 to 2.5 gallons of water to make an aqueous composition, resembling a milkshake, ready for warming before usage. In the set up procedure however, two of these "single packs" are used with the volume of water normally employed with a single pack, to create a "starter" slurry. Thereafter, replenishment takes place by the addition of a "single pack" with the normal amount of water used therewith.

Since certain changes may be made in the above process and composition without departing from the scope of the invention herein involved, it is intended that all matter contained in the above description shall be interpreted as illustrative and not in a limiting sense.

I claim:

1. A composition for use in the practice of body wrapping, which composition when applied to the skin of a human will extract waste products and toxins through the pores, and which composition comprises:

| INGREDIENT | PARTS BY VOLUME |
| --- | --- |
| Clay | |
| Bentonite | 0 to 2.5 |
| Montmorillonite | 2.5 to 0 |
| Sodium Chloride | ¼ to ¾ |
| Magnesium chloride | ¾ to 1.25 |
| Magnesium Sulfate | 1.5 to 2.5 |
| Zinc Oxide | less than .001 |
| Water | 1.5 to 2.5 | wherein the total bentonite-montmorillonite clay component is present in at least 1.5 parts.

2. The composition of claim 1 wherein the clay is bentonite.

3. The composition of claim 1 wherein the clay is montmorillonite.

4. A composition for use in the practice of body wrapping, which composition when applied to the skin of a human will extract waste products and toxins through the pores, and which composition comprises:

| INGREDIENT | PARTS BY VOLUME |
|---|---|
| a clay selected from the group consisting of bentonite and montmorillonite | about 2 |
| Magnesium sulfate | about 2 |
| Magnesium chloride | about 1 |
| Sodium chloride | about ½ |
| Zinc oxide | a minor amount |
| Water | an amount suitable for slurry formation |

5. A composition as in claim 1 wherein all of the ingredients except the water, are present in double quantities.

6. The process of wrapping all or part of the body with elastic bandages to remove wastes and toxins which process comprises:
wrapping the body with bandages which have been immersed in a slurry of a composition which comprises:

| INGREDIENT | PARTS BY VOLUME |
|---|---|
| a clay selected from the group consisting of bentonite and montmorillonite | about 2 |
| Magnesium sulfate | about 2 |
| Magnesium chloride | about 1 |
| Sodium chloride | about ½ |
| Zinc oxide | a minor amount |
| Water | an amount suitable for slurry formation |

7. The process of wrapping all or part of the body with elastic bandages to remove wastes and toxins which comprises:
wrapping the body with bandages which have been immersed in a slurry of a composition which comprises:

| INGREDIENT | PARTS BY VOLUME |
|---|---|
| Clay | |
| Bentonite | 0 to 2.5 |
| Montmorillonite | 2.5 to 0 |
| sodium chloride | ¼ to ¾ |
| Magnesium chloride | ¾ to 1.25 |
| Magnesium sulfate | 1.5 to 3.5 |
| Zinc oxide | less than .001 |

* * * * *